(12) United States Patent
Zhang et al.

(10) Patent No.: US 11,906,401 B2
(45) Date of Patent: Feb. 20, 2024

(54) SAMPLING DEVICE FOR GEOLOGICAL FLUID DETECTION

(71) Applicant: Chengdu University of Technology, Chengdu (CN)

(72) Inventors: Chen Zhang, Chengdu (CN); Huaguo Wen, Chengdu (CN); Chao Ma, Chengdu (CN); Jintong Liang, Chengdu (CN); Yiquan Ma, Chengdu (CN); Yixin Dong, Chengdu (CN); Shaohui Wang, Chengdu (CN); Gang Zhou, Chengdu (CN); Yuan Zhong, Chengdu (CN); Wenbin Tang, Chengdu (CN); Bolin Zhang, Chengdu (CN); Yiting Sun, Chengdu (CN); Yunchuan Zeng, Chengdu (CN)

(73) Assignee: Chengdu University of Technology, Chengdu (CN)

( * ) Notice: Subject to any disclaimer, the term of this patent is extended or adjusted under 35 U.S.C. 154(b) by 0 days.

(21) Appl. No.: 18/353,053

(22) Filed: Jul. 14, 2023

(65) Prior Publication Data
US 2023/0366787 A1    Nov. 16, 2023

(30) Foreign Application Priority Data
May 16, 2022    (CN) .......................... 202210525468.7

(51) Int. Cl.
G01N 1/16    (2006.01)
G01N 1/12    (2006.01)
G01N 1/10    (2006.01)

(52) U.S. Cl.
CPC ................. G01N 1/16 (2013.01); G01N 1/12 (2013.01); G01N 2001/1031 (2013.01)

(58) Field of Classification Search
CPC .... G01N 1/16; G01N 1/12; G01N 2001/1031; G01N 1/14
USPC .............. 73/864.34, 864.51, 864.73, 864.74, 73/864.81
See application file for complete search history.

(56) References Cited

FOREIGN PATENT DOCUMENTS

| CN | 105556315 | A | 5/2016 |
| CN | 109580295 | A | 4/2019 |
| CN | 214844214 | U | * 11/2021 |
| CN | 114112541 | A | 3/2022 |

* cited by examiner

Primary Examiner — Robert R Raevis
(74) Attorney, Agent, or Firm — Nitin Kaushik

(57) ABSTRACT

The invention provides a sampling device for geological fluid detection, relates to the technical field of fluid detection. The sampling device comprises a support frame, the support frame is of an L-shaped structure, and a second support plate is arranged at an upper portion of the support frame; the protection cover is mounted at the corner of a bottom portion of the support frame. The water fixing member is clamped above the bottom portion of the support frame; the locking inclined block is mounted at the bottom portion of the; and the detector is provided with a water inlet pipe. Fluid at different depths is detected through cooperation of the mounting sleeve and the lifting frame, a fluid drainage tube is wound around the winding wheel, the mounting sleeve is driven by the lifting frame to adjust the position through the arrangement of the gear and the rack, the fluid is sampled through the sampling test tube.

9 Claims, 10 Drawing Sheets

SAMPLING DEVICE FOR GEOLOGICAL FLUID DETECTION

CROSS-REFERENCE TO RELATED APPLICATIONS

The application claims priority to Chinese patent application No. 2022105254687, filed on May 16, 2022, the entire contents of which are incorporated herein by reference.

TECHNICAL FIELD

The present invention pertains to the field of fluid detection technology, and more specifically, relates to a sampling device for geological fluid detection.

BACKGROUND

Fluids include geological fluids, and geological fluids refer to rainwater and naturally formed fluids. In order to use and observe fluids, the geological fluid detection is required, and a sampling device will be used in the geological fluid detection, and a detection device will be also used to facilitate the fluid detection.

In the detection of fluids at different depths, the detection head of the detection device needs to be controlled to lift, and since the detection device needs to detect the depth, the relatively long drainage tube will be arranged, and the drainage tube will become loose during the lifting of the detection device, thus affecting the use of the drainage tube, and the storage of the drainage tube and the adjustment of the detection position need to be operated separately, which not only makes the structure of the detection device complex, but also makes the operation of the detection device troublesome; in the process of fluid detection, a sampling device needs to be arranged for separate operation, which not only increases the labor force, but also increases the overall cost and weight, causing the problem of inconvenience in carrying the whole, and different test tubes are used for fluid sampling at different depths, which has the problem of inconvenience in switching test tubes and also affects the carrying of test tubes.

SUMMARY

In order to solve the above technical problems, the present invention provides a sampling device for geological fluid detection to solve the problem that the drainage tube will become loose during the lifting of the detection device, the storage of the drainage tube and the adjustment of the detection position need to be operated separately, the sampling device is operated separately, causing the inconvenience of overall carrying and the test tube switching.

The purpose and efficacy of the sampling device for geological fluid detection of the present invention is achieved by the following specific technical means:

A sampling device for geological fluid detection, comprising a support frame;
The support frame is of an L-shaped structure, and a second support plate is arranged at an upper portion of the support frame;
A protective cover, the protection cover is mounted at a corner of a bottom portion of the support frame;
Fixing members, the fixing members are clamped above the bottom portion of the support frame; a locking inclined block, the locking inclined block is mounted at the upper part of the bottom portion of the support frame;
A detector, the detector is provided with a water inlet pipe, the detector is clamped to the second support plate of the support frame;
A mounting sleeve, the mounting sleeve is clamped to the bottom of the upper portion of the support frame, a hose is mounted between the water inlet pipe of the detector and the mounting sleeve, a test strip is mounted above the detector; a positioning seat, the positioning seat is bolted to the bottom of the upper portion of the support frame;
A drive mechanism, the drive mechanism is mounted on the outside of the support frame;
A loading tray, the loading tray is mounted on the outside of the support frame; a sampling test tube, the sampling test tube is clamped to the inside of the loading tray.

Preferably, the support frame comprises:
a support block, the support block is arranged above the support frame, and the support block is provided with two mounting holes;
A threaded telescopic tube, the threaded telescopic tube is arranged above the support frame, the support frame is provided with two insertion holes communicated with the threaded telescopic tube, and the fixing members fit into the insertion holes in the support frame;
A first support plate, the first support plate is of an L-shaped structure, the first support plate is on the outside of the support frame, the first support plate is provided with a positioning hole, and the positioning hole is of a rectangular structure.

Preferably, there are two fixing members in total with a connecting plate between the two fixing members, and the fixing members are clamped to the inside of the threaded telescopic tube.

Preferably, the locking inclined block comprises:
sliding rods, the sliding rods are on the outside of the locking inclined block, there are two sliding rods, a second support spring is sleeved on the outside of the sliding rod, and a friction block of circular structure is arranged above the locking inclined block.

Preferably, the mounting sleeve has two locking clasps on the outside, and the locking clasp of the mounting sleeve has a breakout block on the outside.

Preferably, the positioning seat comprises:
a first positioning block, the first positioning block is of a rectangular structure, a mounting slot of the rectangular structure is mounted at the bottom of the support frame, the first positioning block is clamped in the mounting slot of the support frame, and the first positioning block is provided with a threaded slot.

Preferably, the drive mechanism comprises:
a winding wheel, a bevel gear disk is mounted on the outside of the winding wheel, and the winding wheel is mounted on the outside of the support frame;
a first rotation shaft, a first bevel gear is respectively mounted at both ends of the first rotation shaft, and the first bevel gear at the upper end engages with the bevel gear disk;
a second rotation shaft, a second bevel gear is mounted at the end of the second rotation shaft, the second bevel gear engages with the first bevel gear, and a toggle gear is mounted on the outside of the second rotation shaft;
a lifting frame, a rack is mounted on the outside of the lifting frame, and the rack engages with the toggle gear.

Preferably, the protective cover is provided with a sliding hole, the first rotation shaft is inserted in the sliding hole of the protective cover, an anti-loosening plate is on the outside of the protective cover, the anti-loosening plate is of a rectangular structure, the support frame is provided with two vertical positioning slots at the bottom, the protective cover is clamped in the positioning slots of the support frame, and a first support spring is sleeved on the outside of the first rotation shaft.

Preferably, the lifting frame comprises:
a mounting block, the mounting sleeve is provided with an annular groove, the mounting block is clamped in the annular groove of the mounting sleeve, the mounting block has a mounting groove on the inside, and an inclined surface on the outside.

Preferably, the loading tray is provided with four mounting holes distributed in a cross shape, the sampling test tube is clamped in the mounting holes of the loading tray, and the detector has a bent neck on the outside.

Preferably, the loading tray comprises:
a second positioning block, the second positioning block is at the bottom of the loading tray, the second positioning block is of a rectangular structure, and the second positioning block is clamped in a positioning hole of the first support plate;
a third positioning block, the third positioning block is of a cylindrical structure, and the third positioning block is at the bottom of the second positioning block (901).

Compared with the prior art, the present invention has the following beneficial effects:

1. The mounting sleeve works with the lifting frame to detect the fluid at different depths, solving the problem of inconvenient detection of fluid at different depths, the fluid drainage tube of the fluid is wound around the winding wheel, solving the problem of inconvenient storage of the excessively long fluid drainage tube, the gear and the rack are arranged to solve the problem of driving the lifting frame up and down in the process of winding of the winding wheel, and the mounting sleeve is driven by the lifting frame for position adjustment.
2. The sampling tube is used for the fluid sampling, a bent neck is arranged for the detector, so that the detection fluid in the detector can directly enters into the sampling tube, solving the problem of rapid sampling of fluid, the detector and test paper are used for double detection of fluid, improving the efficiency of fluid sampling, the loading tray is used to for the position switching of the sampling tube, solving the problem of inconvenience in switching the sampling tube and the problem of inconvenience in fluid carrying.
3. The mounting sleeve is arranged to facilitate the installation of the drainage hose, and the locking clasp is arranged on the outside of the mounting sleeve to solve the problem of unstable installation of the drainage hose, the fixing member is used to reinforce the whole, the locking inclined block is used to lock the downwardly moved fixing member, the threaded telescopic tube is used to support the fixing member elastically, solving the problem of pulling out the fixing member with great effort, and the problem of soil cleaning on the outside of the fixing member is solved by the through holes set in the support frame.
4. The loading tray is set as elastically connected, which solves the problem of automatic reset after the position of sampling test tube is switched, and the gear is protected by the protective cover, and the protective cover is provided with the anti-loosening plate to prevent loosening.

EXPLANATION OF NUMBERS MARKED IN THE FIGURE

1—Support frame; 101—Support block; 102—Threaded telescopic tube; 103—First support plate; 2—Protective cover; 3—Fixing member; 4—Locking inclined block; 401—Sliding rod; 5—Detector; 6—Mounting sleeve; 7—Positioning seat; 701—First positioning block; 8—Drive mechanism; 801—Winding wheel; 802—First rotation shaft; 803—Second rotation shaft; 804—Lifting frame; 80401—Mounting block; 9—Loading tray; 901—Second positioning block; 902—Third positioning block; 10—Sampling test tube; 402—friction block; 602—locking clasps; 202—anti-loosening plate; 501—water inlet pipe; 502—fluid drainage tube/hose; 806—bevel gear disk; 808A, 808B—first bevel gears; 810—second bevel gear; 814—rack; 812—toggle gear; 104—vertical positioning slot; 702—fixing bolts; 606—annular groove; 80402—mounting groove; 80403—inclined surface; 301—connecting plate; 503—test strip/test paper; 105—insertion holes; 903—mounting holes; 106—second support plate.

DETAILED DESCRIPTION OF THE EMBODIMENTS

The embodiments of the present invention will be further described in details in conjunction with the accompanying drawings and embodiments. The following embodiments are intended to explain the present invention, but cannot be used to limit the scope of the present invention.

Figure 1:
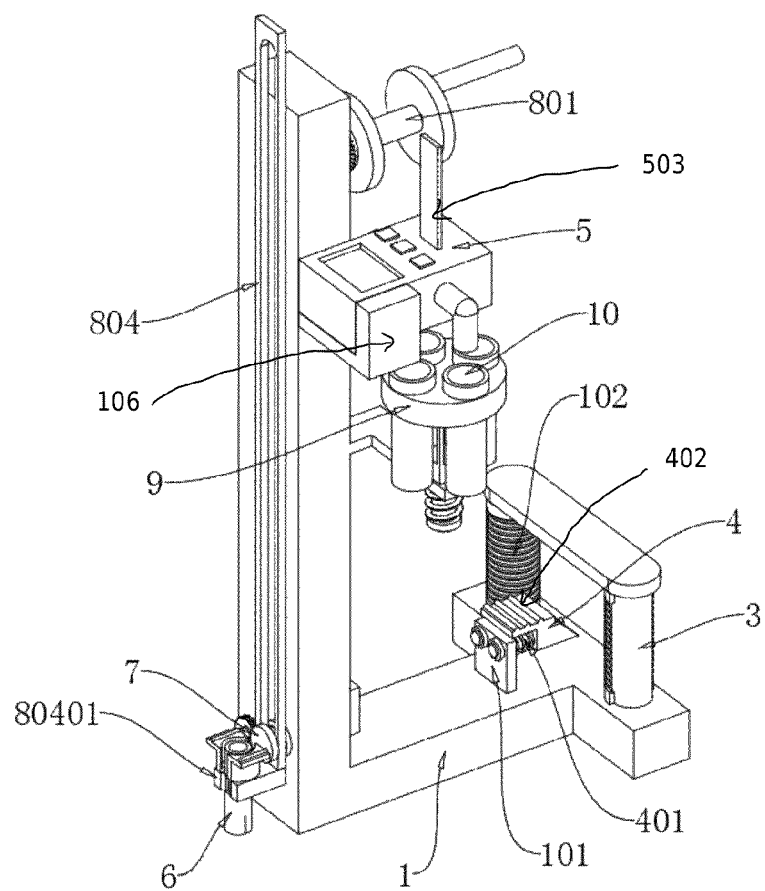
FIG. 1 is a schematic diagram of the shaft side structure of the main body of the present invention.
Figure 2:
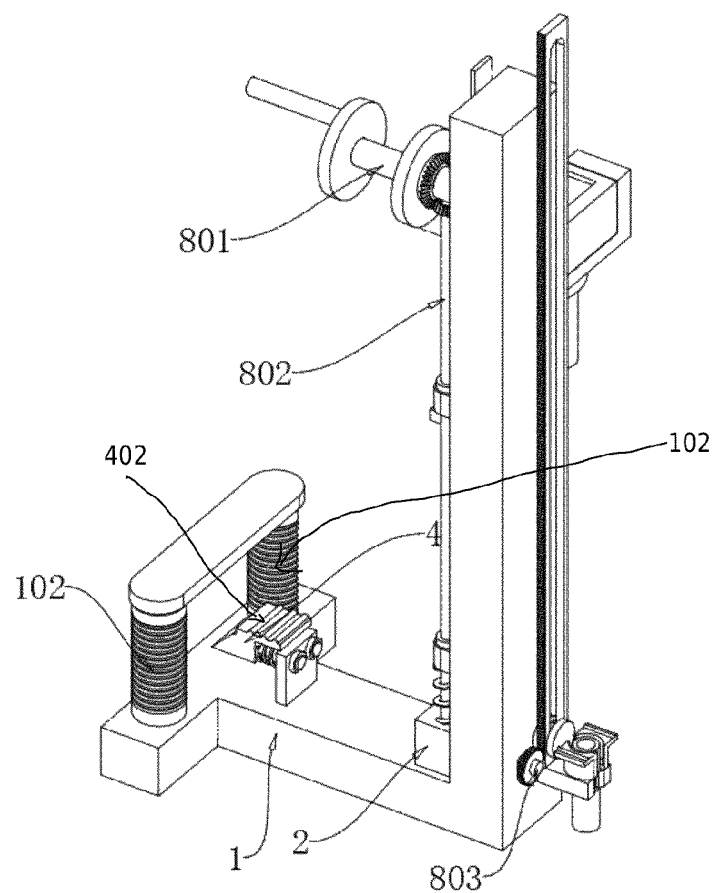
FIG. 2 is a rear-view schematic diagram of the shaft side structure of FIG. 1 of the present invention.
Figure 3:
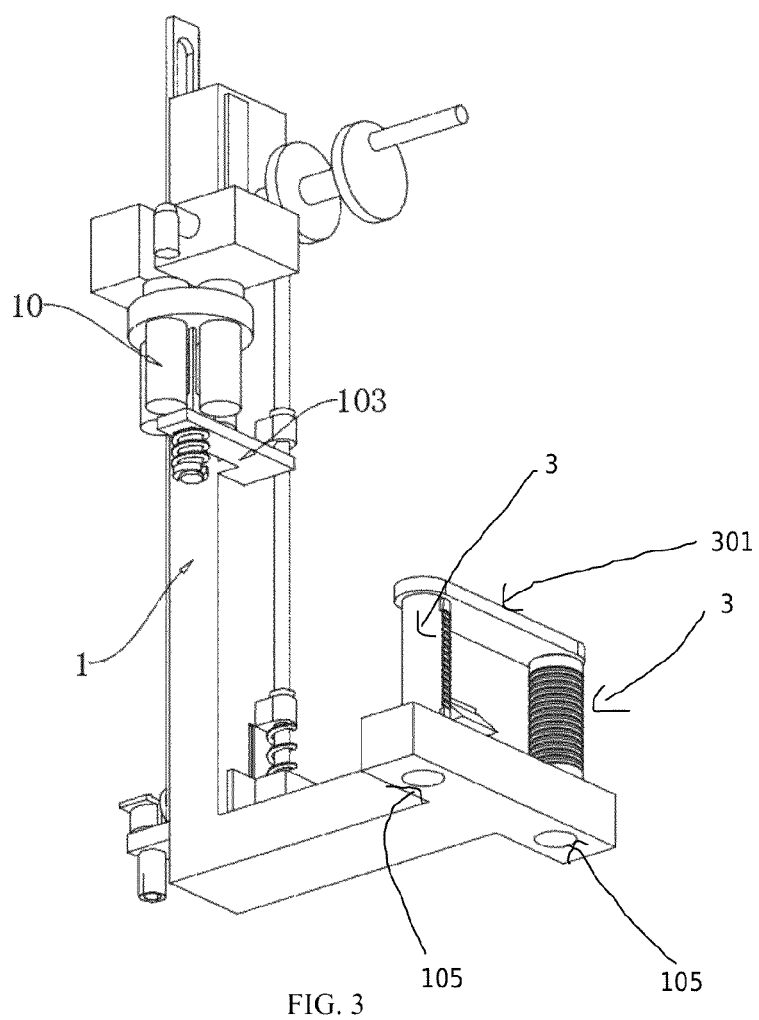
FIG. 3 is an elevation-view schematic diagram of the shaft side structure of FIG. 1 of the present invention
Figure 4:
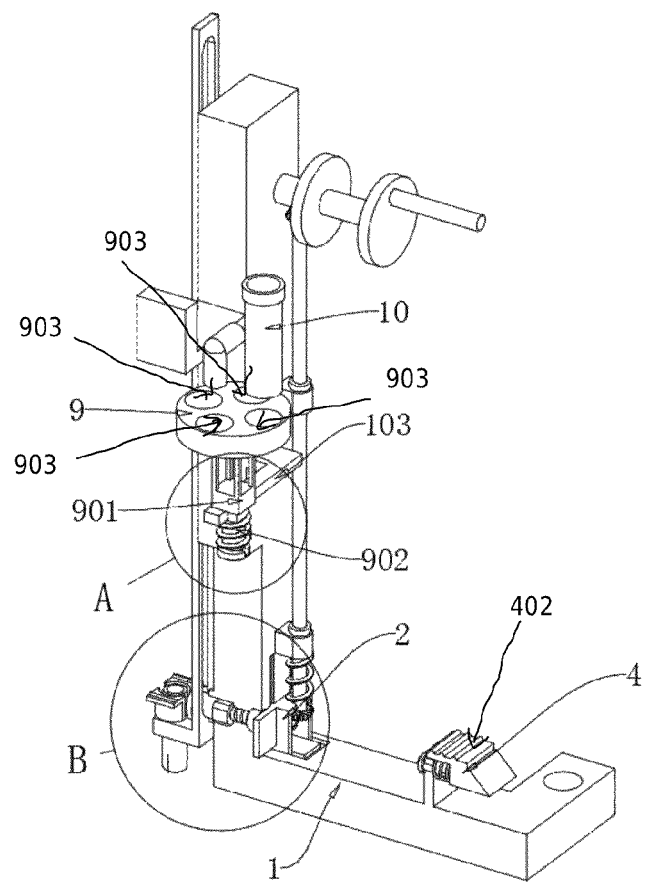
FIG. 4 is a sectional schematic diagram of the shaft side structure of the support frame of the present invention.
Figure 5:
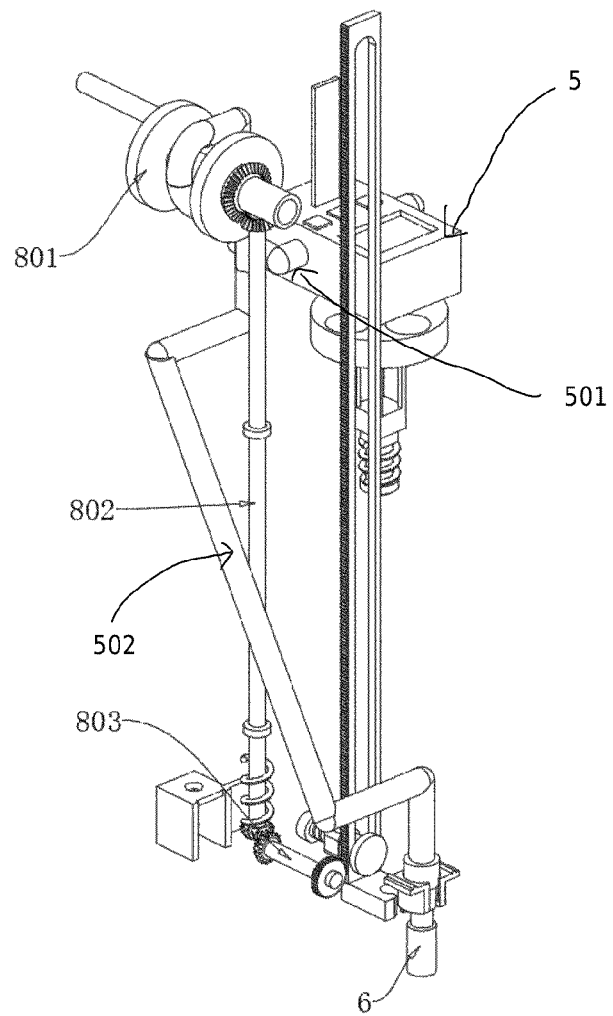
FIG. 5 is a schematic diagram of the shaft side structure of the present invention with the support frame removed.
Figure 6:
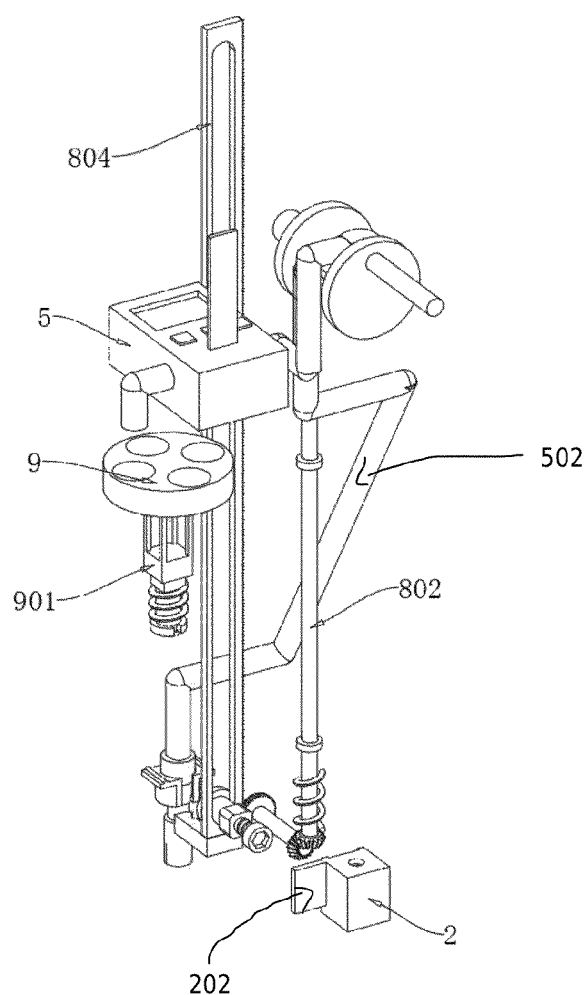
FIG. 6 is a right-view schematic diagram of the shaft side structure of FIG. 5 of the present invention.
Figure 7:
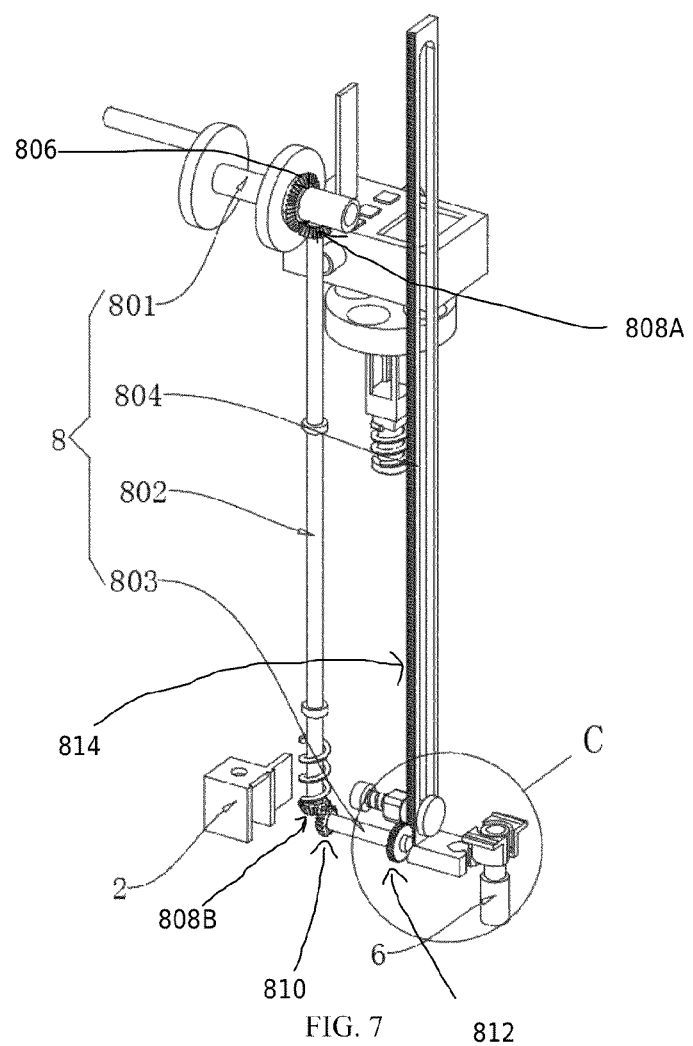
FIG. 7 is a schematic diagram of the shaft side structure of FIG. 5 of the present invention with the hose removed.
Figure 8:
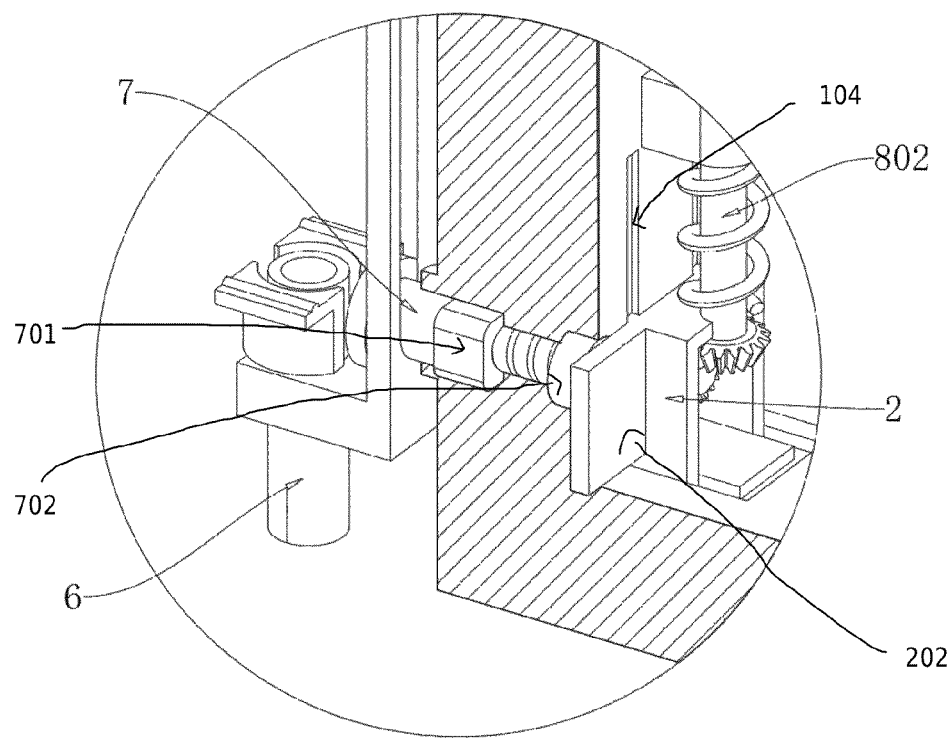
FIG. 8 is a schematic diagram of the enlarged structure at A of FIG. 4 of the present invention.
Figure 9:
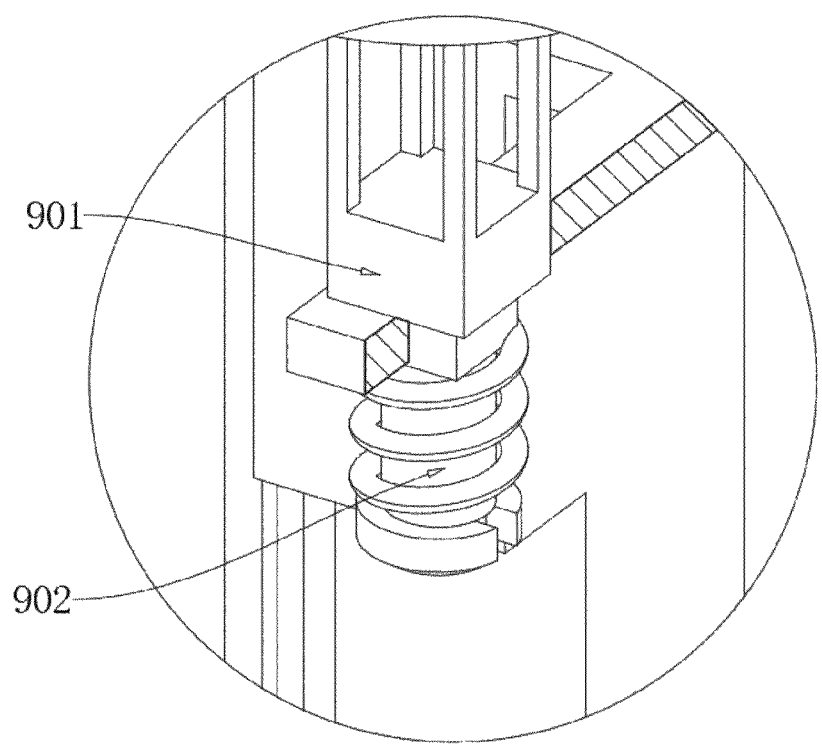
FIG. 9 is a schematic diagram of the enlarged structure at B of FIG. 4 of the present invention.
Figure 10:
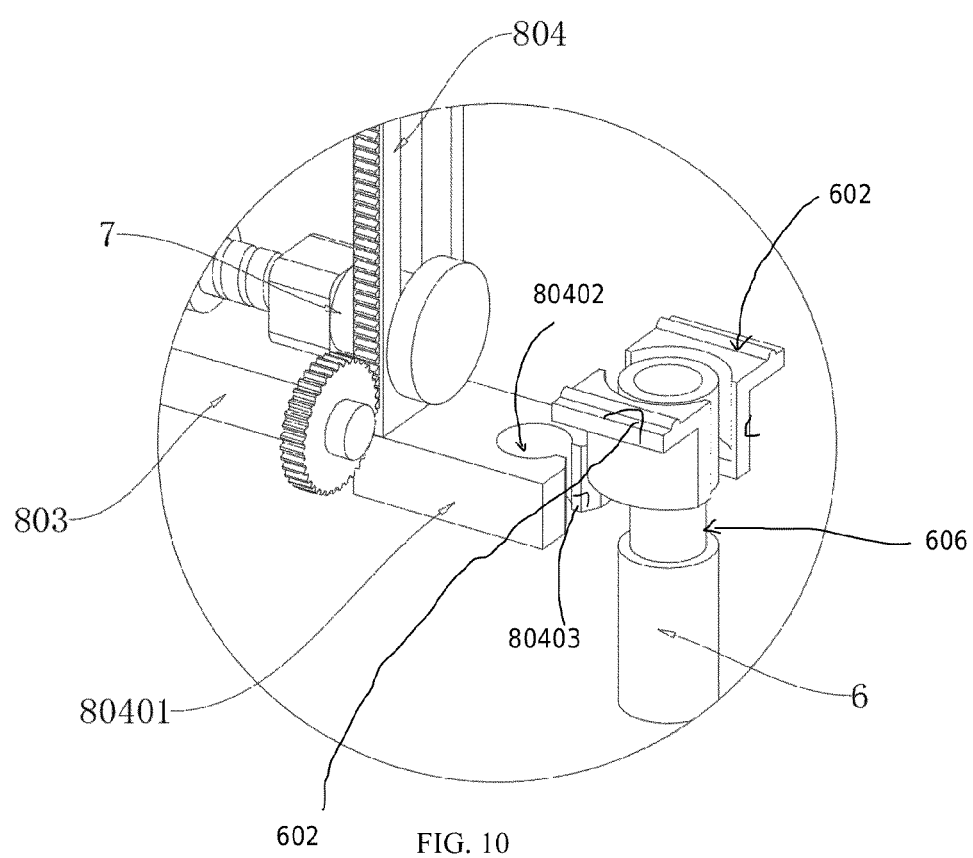
FIG. 10 is a schematic diagram of the enlarged structure at C of FIG. 7 of the present invention.

As shown in the FIG. 1 to FIG. 10:

The present invention provides a sampling device for geological fluid detection, comprising a support frame 1;

The support frame 1 is of an L-shaped structure, the support frame 1 supports the whole; The support frame 1 comprises an upper portion and a bottom portion; a second support plate 106 is arranged at the upper portion of the support frame 1, and the second support plate 106 supports and positions the detector 5; the support frame 1 comprises a support block 101, a threaded telescopic tube 102 and a first support plate 103, wherein the support block 101 is arranged above at the bottom portion of the support frame 1, the support block 101 is provided with two mounting holes, the support block 101 supports the sliding rod 401, and the mounting holes of the support block 101 position the sliding rod 401; the threaded telescopic tube 102 is arranged above at the bottom portion of the support frame 1, and the threaded telescopic tube 102 supports the fixing member 3 upward elastically so that the fixing member 3 is automatically reset for concealment, the support frame 1 is provided with two insertion holes 105 communicated with the threaded telescopic tube 102, the fixing member 3 slides in the insertion holes 105 of 105 of the support frame 1, and when the fixing member 3 slides in the insertion holes 105 of the support frame 1, the insertion holes 105 will erase the soil adhering to the outside of the fixing member 3; the first support plate 103 is of an L-shaped structure, the first support plate 103 is on the outside of the support frame 1, the first support plate 103 is provided with a positioning hole, the positioning hole is of a rectangular structure, the positioning hole positions the second positioning block 901, and the first support plate 103 supports the loading tray 9;

A protective cover 2, the protective cover 2 is mounted at the corner of the bottom portion of the support frame 1, the protective cover 2 is provided with a sliding hole, the first rotation shaft 802 is inserted in the sliding hole of the protective cover 2, the first rotation shaft 802 positions the protective cover 2, the protective cover 2 protects the bevel gear between the first rotation shaft 802 and the second rotation shaft 803, an anti-loosening plate 202 is on the outside of the protective cover 2, the anti-loosening plate 202 is of a rectangular structure, the anti-loosening plate 202 covers the fixing bolts 702 of the positioning seat 7, so that the anti-loosening plate 202 prevents the fixing bolts 702 of the positioning seat 7 from loosening to avoid the loosening of the fixing bolts 702 of the positioning seat 7, and the protective cover 2 slides up and down through the sliding holes, so as to facilitate the installation and removal of the fixing bolts 702 of the positioning seat 7, the support frame 1 is provided with two vertical positioning slots 104 at the bottom, and the protective cover 2 is clamped in the positioning slots 104 of the support frame 1, and the positioning slots 104 of the support frame 1 circumferentially position the protective cover 2, a first support spring is sleeved on the outside of the first rotation shaft 802, the first support spring elastically supports the protective cover 2 downward, so that the protective cover 2 stably protects the bevel gear;

Fixing members 3, the water fixing members 3 are clamped to the support frame 1, and there are two fixing members 3 in total with a connecting plate 301 between the two fixing members 3, the two fixing members 3 are driven to move at the same time through the connecting plate 301, and the fixing members are clamped to the inside of the threaded telescopic tube 102, the threaded telescopic tube 102 will be squeezed when the fixing member moves downwards, and the fixing members 3 are inserted into the soft ground to reinforce the whole;

A locking inclined block 4, the locking inclined block 4 is mounted above at the bottom portion of the support frame 1, and the locking inclined block 4 comprises a sliding rod 401, the sliding rod 401 is on the outside of the locking inclined block 4, there are two sliding rods 401, two sliding rods 401 circumferentially position the locking inclined block 4, a second support spring is sleeved on the outside of the sliding rod 401, the second support spring elastically supports the locking inclined block 4, so that the locking inclined block 4 automatically resets; the locking inclined block 4 locks the downwardly pressed fixing member 3, so that the fixing member 3 is firmly inserted into the bottom surface; a friction block 402 of circular structure is arranged above the locking inclined block 4, and the friction block 402 facilitates pushing on the locking inclined block 4, and after pushing the locking inclined block 4, the fixing member 3 slides upward and resets, and in the process of downward movement of the fixing member 3, the fixing member 3 automatically locks the connecting plate 301 of the fixing member 3, so as to facilitate the operation of the fixing member 3;

A detector 5, the detector 5 is provided with a water inlet pipe 501, and the detector 5 is clamped to the inside of the second support plate 106 of the support frame 1;

A mounting sleeve 6, the mounting sleeve 6 is clamped to the bottom of the upper portion of the support frame 1, a hose 502 is mounted between the water inlet pipe 501 of the detector 5 and the mounting sleeve 6, the fluid is delivered into the detector 5 for detection via the hose 502, a test strip is mounted above the detector 5, the fluid is detected via the test strip, the mounting sleeve 6 has two locking clasps 602 on the outside, the locking clasps 602 lock the bottom of the hose 502 between the detector 5 and the mounting sleeve 6, so that the hose 502 is firmly connected to the mounting sleeve 6, the locking clasp of the mounting sleeve 6 has a breakout block on the outside, and the locking clasp is broken by the breakout block, so that the bottom hose 502 can be removed;

A positioning seat 7, the positioning seat 7 is bolted to the bottom of the upper portion of the support frame 1, the positioning seat 7 comprises a first positioning block 701, the first positioning block 701 is of a rectangular structure, a mounting slot of the rectangular structure is mounted at the bottom of the support frame 1, the first positioning block 701 is clamped in the mounting slot of the support frame 1, the mounting slot of the support frame 1 is hidden to the first positioning block 701, the first positioning block 701 circumferentially positions the positioning seat 7, the first positioning block 701 is provided with a threaded slot, and the threaded slot is used to connect the fixing bolt 702 of the first positioning block 701;

A drive mechanism 8, the drive mechanism 8 is mounted on the outside of the support frame 1, the drive mechanism 8 consists of a winding wheel 801, a first rotation shaft 802, a second rotation shaft 803, a lifting frame 804 and a mounting block 80401 together, a bevel gear disk 806 is mounted on the outside of the winding wheel 801, and the bevel gear disk 806 is driven to rotate when the winding wheel 801 rotates, and the hose 502 is wound around the winding wheel 801, the winding wheel 801 is mounted on the outside of the support frame 1, and first bevel gears 808A, 808B are mounted respectively at both ends of the first rotation shaft 802, and the first bevel gear 808A at the upper end of the first rotation shaft 802 engages with the bevel gear disk 806, so that the first rotation shaft 802 will be driven to rotate when the winding wheel 801 rotates, and a second bevel gear 810 is mounted at the end of the second rotation shaft 803, and the second bevel gear 810 engages with a first bevel gear 808B, so that the second rotation shaft 803 will be driven to rotate when the first rotation shaft 802 rotates, and a toggle gear 812 is mounted on the outside of the second rotation shaft 803, and the toggle gear 812 will be driven to rotate when the second rotation shaft 803 rotates, and the lifting frame 804 has a rack 814 on the outside, and the rack 814 engages with the toggle gear 812, and the lifting frame 804 will be pushed up and down when the toggle gear 812 rotates, the mounting sleeve 6 has an annular groove 606, the mounting block 80401 is clamped in the annular groove 606 of the mounting sleeve 6, the inclined surface 80403 facilitates the installation of the mounting sleeve 6, the mounting block 80401 will be driven to move when the lifting frame 8044 moves, so that the mounting sleeve 6 will be driven by the mounting block 80401 to move, and the position of mounting sleeve 6 will be adjusted;

A loading tray 9, the loading tray 9 is mounted on the outside of the support frame 1, the loading tray 9 comprises a second positioning block 901 and a third positioning block 902, the second positioning block 901 is at the bottom of the loading tray 9, the second positioning block 901 is of a rectangular structure, the second positioning block 901 positions the loading tray 9 at ninety degrees, and the second positioning block 901 is clamped in the positioning hole of the first support plate 103; the third positioning block 902 is of a cylindrical structure, the third positioning block 902 is at the bottom of the second positioning block 901, after the loading tray 9 is pulled upward, the third positioning block 902 facilitates the rotation of the loading tray 9, thus facilitating the loading tray 9 to drive the sampling test tube 10 for position switching;

A sampling test tube 10, the loading tray 9 is provided with four mounting holes 903 distributed in a cross shape, the sampling test tube 10 is clamped in the mounting holes 903 of the loading tray 9, the mounting holes 903 of the loading tray 9 position the sampling test tube 10, the sampling test tube 10 stores the geological fluid after sampling, the detector 5 has a bent neck on the outside, the geological fluid in the detector 5 flows through the bent neck to the outside, and the bent neck is orthogonal to the sampling test tube 10, so that the fluid of the detector 5 enters directly into the sampling test tube 10 during the detection, thus facilitating the sampling of the fluid.

In another embodiment, the second support plate 106 on the outside of the support frame 1 is set to be elastically connected, so that the second support plate 106 clamps and locks the different sizes of the detector 5, the micro pump is mounted inside the detector 5, and the fluid is pumped by the micro pump.

The specific use and function of this embodiment are as follows:

In use, the fixing member 3 is first mounted on the inside of the threaded telescopic tube 102 to complete the positioning and support of the threaded telescopic tube 102, the drive mechanism 8 is mounted on the outside of the support frame 1, and then the detector 5 is mounted on the inside of the second support plate 106 to complete the installation of the detector 5, the sampling test tube 10 is placed on the inside of the loading tray 9, the invention is placed to the position where fluid detection is needed, and the support frame 1 supports the whole, and when the detection is performed on the soft ground, the fixing member 3 is stepped down to reinforce the support frame 1, and when the fixing member 3 is pulled out, the locking inclined block 4 is first pushed, and at the moment the fixing member 3 is reset by moving upwards with the help of the threaded telescopic tube 102;

In the underground fluid detection, the test paper 503 is first clamped on the inside of the detector 5 for double detection of the fluid through the detector (5) and the test paper 503, the winding wheel 801 is rotated to drive the first rotation shaft 802 and the second rotation shaft 803 to rotate, so that the second rotation shaft 803 drives the lifting frame 804 to move downward, the lifting frame 804 drives the mounting sleeve 6 for position adjustment; when the mounting sleeve 6 moves to the position to be detected, the rotation of the winding wheel 801 is stopped, and the fluid is pumped through the detector 5, and the geological fluid inside the detector 5 flows through the bent neck to the outside, and the bent neck is orthogonal to the sampling test tube 10, so that the fluid of the detector 5 enters directly into the sampling test tube 10 during the detection, thus facilitating the sampling of the fluid;

In the detection of fluids at different depths, the position of the mounting sleeve 6 is adjusted, while the position of the sampling test tube 10 is replaced, during the position replacement of the sampling test tube 10, the loading tray 9 is first pressed downward, and then the loading tray 9 is rotated for ninety degrees to switch the sampling test tube 10, the different sampling test tubes 10 are used for sampling the fluid at different depths, and the sampling test tube 10 and detector 5 work together for the better detection of the fluid;

After the fluid detection is completed, the winding wheel 801 is reversed, and at this time the winding wheel 801 winds the hose 502, while the lifting frame 804 drives the mounting sleeve 6 move upward for storage.

The embodiments of the present invention are given for purposes of example and description, and are not intended to be without omission or to limit the invention to the disclosed form. Many modifications and variations will be apparent to those of ordinary skill in the art. The embodiments have been selected and described to better illustrate the principles and practical applications of the invention, and various embodiments with various modifications suitable for particular uses have been designed to enable those of ordinary skill in the art to understand the invention.

What is claimed is:

1. A sampling device for geological fluid detection, comprising:
    a support frame (1) having an L-shaped structure with an upper portion and a bottom portion;
    a second support plate (106) is arranged at the upper portion of the support frame (1);
    a protective cover (2), the protective cover (2) is mounted at the bottom portion of the support frame (1);
    fixing members (3), wherein the fixing members (3) are mounted above at the bottom portion of the support frame (1), and there are two fixing members (3) with a connecting plate (301) between the two fixing members (3);
    a locking inclined block (4), the locking inclined block (4) is mounted at the bottom portion of the support frame (1);
    a detector (5), the detector (5) is provided with a water inlet pipe (501), and the detector (5) is clamped to the second support plate (106) of the support frame (1);
    a mounting sleeve (6), the mounting sleeve (6) is clamped to a bottom of the upper portion of the support frame (1), a fluid drainage tube (502) is mounted between the water inlet pipe (501) of the detector (5) and the mounting sleeve (6), a test strip (503) is mounted above the detector (5) for double detection of the fluid through the detector (5) and the test strip (503);

a positioning seat (7), the positioning seat (7) is bolted to the bottom of the upper portion of the support frame (1);

a drive mechanism (8), the drive mechanism (8) consists of a winding wheel (801), a first rotation shaft (802), a second rotation shaft (803), a lifting frame (804) and a mounting block (80401) together, a bevel gear disk (806) is mounted on a side of the winding wheel (801), and the bevel gear disk (806) is driven to rotate when the winding wheel (801) rotates, and a portion of the fluid drainage tube (502) is wound around the winding wheel (801), the winding wheel (801) is mounted to the support frame (1), and two first bevel gears (808A, 808B) are mounted respectively at both ends of the first rotation shaft (802), and one of the two first bevel gears (808A) at an upper end of the first rotation shaft (802) engages with the bevel gear disk (806), so that the first rotation shaft (802) will be driven to rotate when the winding wheel (801) rotates, and a second bevel gear (810) is mounted at one end of the second rotation shaft (803), and the second bevel gear (810) engages with the other one of the two first bevel gears (808B) at a lower end of the first rotation shaft (802), so that the second rotation shaft (803) will be driven to rotate when the first rotation shaft (802) rotates, and a toggle gear (812) is mounted at an another end of the second rotation shaft (803), and the toggle gear (812) will be driven to rotate when the second rotation shaft (803) rotates, and the lifting frame (804) has a rack (814) on one side, and the rack (814) engages with the toggle gear (812), and the lifting frame (804) will be pushed up and down when the toggle gear (812) rotates, the mounting sleeve (6) has an annular groove (606), the mounting block (80401) is clamped in the annular groove (606) of the mounting sleeve (6), the mounting block (80401) will be driven to move when the lifting frame (8044) moves, so that the mounting sleeve (6) will be driven by the mounting block (80401) to move, and a position of the mounting sleeve (6) will be adjusted;

a loading tray (9), the loading tray (9) is mounted to the support frame (1); and a sampling test tube (10), the sampling test tube (10) is arranged in the loading tray (9).

2. The sampling device according to claim 1, wherein the support frame (1) comprises:

a support block (101), the support block (101) is arranged above the bottom portion of the support frame (1), and the support block (101) is provided with two mounting holes;

a threaded telescopic tube (102), the threaded telescopic tube (102) is arranged above the bottom portion of the support frame (1), the support frame (1) is provided with two insertion holes communicated with the threaded telescopic tube (102), and the fixing members (3) fit into the two insertion holes in the support frame (1);

a first support plate (103), the first support plate (103) is of an L-shaped structure, the first support plate (103) is mounted to the upper portion of the support frame (1), and the first support plate (103) is provided with a positioning hole.

3. The sampling device according to claim 1, wherein the sampling device comprises:

sliding rods (401), the sliding rods (401) are under the locking inclined block (4), there are two sliding rods (401);

a second support spring is sleeved on an outside of each sliding rod (401); and a friction structure (402) is arranged above the locking inclined block (4).

4. The sampling device according to claim 1, wherein the mounting sleeve (6) has two locking clasps (602) that lock a bottom of the fluid drainage tube (502) between the detector (5) and the mounting sleeve (6), so that the fluid drainage tube (502) is firmly connected to the mounting sleeve (6).

5. The sampling device according to claim 1, wherein the positioning seat (7) comprises:

a first positioning block (701), the first positioning block (701) is of a rectangular structure, wherein the support frame (1) comprises a mounting slot, the first positioning block (701) is clamped to the support frame (1) via the mounting slot.

6. The sampling device according to claim 1, wherein the protective cover (2) is provided with a sliding hole, the first rotation shaft (802) is inserted in the sliding hole of the protective cover (2), an anti-loosening plate (202) is with the protective cover (2), the support frame (1) is provided with two vertical positioning slots (104) at the bottom of the upper portion of the support frame (1), the protective cover (2) is clamped in the vertical positioning slots (104) of the support frame (1), and a first support spring is sleeved on the outside of the first rotation shaft (802), wherein the anti-loosening plate (202) prevents fixing bolts (702) of the positioning seat (7) from loosening.

7. The sampling device according to claim 1, wherein— the mounting block (80401) has a mounting groove (80402) on the inside, and an inclined surface (80403) on the outside.

8. The sampling device according to claim 1, wherein the loading tray (9) is provided with four mounting holes (903) distributed in a cross shape, the sampling test tube (10) is clamped in the mounting holes (903) of the loading tray (9), and the detector (5) has a bent neck on the outside.

9. The sampling device according to claim 1, wherein the loading tray (9) comprises:

a second positioning block (901), the second positioning block (901) is at a bottom of the loading tray (9), the second positioning block (901) is of a rectangular structure, and the second positioning block (901) is clamped in a positioning hole of the first support plate (103);

a third positioning block (902), the third positioning block (902) is of a cylindrical structure, and the third positioning block (902) is at a bottom of the second positioning block (901).

* * * * *